United States Patent [19]

Beech, Jr. et al.

[11] Patent Number: 5,405,814
[45] Date of Patent: Apr. 11, 1995

[54] OLEFIN CONVERSION CATALYST REGENERATION

[75] Inventors: James H. Beech, Jr., Wilmington, Del.; Weldon K. Bell, Pennington, N.J.; W. Thomas Mo, Mt. Laurel, N.J.; Hye Kyung C. Timken, Woodbury, N.J.; Robert A. Ware, Wyndmoor, Pa.

[73] Assignee: Mobil Oil Corporation, Fairfax, Va.

[21] Appl. No.: 72,379

[22] Filed: Jun. 7, 1993

Related U.S. Application Data

[63] Continuation-in-part of Ser. No. 897,156, Jun. 11, 1992, abandoned, which is a continuation-in-part of Ser. No. 557,241, Jul. 25, 1990, Pat. No. 5,162,591, and a continuation-in-part of Ser. No. 794,634, Nov. 18, 1991, Pat. No. 5,138,102, which is a continuation of Ser. No. 557,242, Jul. 25, 1990, abandoned.

[51] Int. Cl.$^6$ .................. B01J 29/38; B01J 38/10; B01J 38/06; C07C 41/05
[52] U.S. Cl. ................................ 502/53; 502/34; 568/694; 568/695; 568/697; 568/897
[58] Field of Search .............. 502/34, 53; 568/694, 568/695, 697, 897

[56] References Cited

U.S. PATENT DOCUMENTS

| | | | |
|---|---|---|---|
| 3,412,013 | 11/1968 | Bowles | 502/53 |
| 4,214,107 | 7/1980 | Chang et al. | 568/897 |
| 4,358,395 | 11/1982 | Haag et al. | 252/411 |
| 4,417,083 | 11/1983 | Bernard et al. | 585/419 |
| 4,499,313 | 2/1985 | Okumura et al. | 568/897 |
| 4,508,836 | 4/1985 | Haag et al. | 502/53 |
| 4,683,052 | 7/1987 | Degnan, Jr. et al. | 208/111 |
| 4,777,156 | 10/1988 | Forbus | 502/53 |
| 4,827,046 | 5/1989 | Harandi et al. | 568/897 |
| 5,015,782 | 5/1991 | Harandi et al. | 568/897 |
| 5,105,023 | 4/1992 | Marcer et al. | 568/897 |
| 5,138,102 | 8/1992 | Beech, Jr. et al. | 568/897 |
| 5,144,084 | 9/1992 | Sorensen et al. | 568/887 |
| 5,151,393 | 9/1992 | Harandi et al. | 502/53 |
| 5,162,591 | 11/1992 | Beech, Jr. et al. | 568/897 |

FOREIGN PATENT DOCUMENTS

| | | | |
|---|---|---|---|
| 3422348 | 12/1985 | Germany | 502/53 |
| 01660 | 2/1929 | WIPO | 568/897 |
| 01661 | 2/1992 | WIPO | 568/897 |

Primary Examiner—Paul E. Konopka
Attorney, Agent, or Firm—Alexander J. McKillop; Malcolm D. Keen; Jessica M. Sinnott

[57] ABSTRACT

An olefin hydration catalyst is regenerated with a non-oxidizing light gas, such as hydrogen. Light olefins, especially propylene, are converted to a mixture of alcohol(s), such as isopropanol (IPA) and ether(s), such as diisopropylether (DIPE) by contacting a feed containing the olefin with water and/or alcohol with the olefin hydration catalyst. Regeneration conditions include temperatures of from about 150° C. to about 550° C., pressures below about 1000 psig (6900 kPa). Lower pressures of regeneration unexpectedly demonstrated more effective catalyst regeneration through greater coke removal.

10 Claims, 7 Drawing Sheets

OLEFIN CONVERSION CATALYST REGENERATION

CROSS REFERENCE TO RELATED APPLICATIONS

This application is a continuation-in-part of Ser. No. 07/897,156, filed on Jun. 11, 1992, which is incorporated herein by reference in its entirety, now abandoned. The benefit of the filing date of Ser. No. 07/897,156 is claimed under 35 U.S.C. §120.

Ser. No. 07/897,156 is a continuation-in-part of Ser. No. 557,241, filed on Jul. 25, 1990, now U.S. Pat. No. 5,162,591, which issued on Nov. 10, 1992.

Ser. No. 07/897,156 is also a continuation-in-part of Ser. No. 794,634, filed on Nov. 18, 1991, now U.S. Pat. No. 5,138,102, which is a continuation of Ser. No. 577,242, filed on Jul. 25, 1990, and now abandoned.

Cross reference is made to Ser. No. 07/798,017 filed on Nov. 20, 1991, now U.S. Pat. No. 5,144,084 which is incorporated by reference in its entirety.

FIELD OF THE INVENTION

This invention relates to a method for regenerating an olefin conversion catalyst. More specifically, the invention concerns the regeneration of an olefin hydration catalyst with a light non-oxidizing gas under regeneration conditions.

BACKGROUND OF THE INVENTION

The manufacture of alcohols and ethers from olefins is an important refinery process since it is favorable to augment the supply of high octane blending stocks for gasoline. Lower molecular weight alcohols and ethers such as isopropyl alcohol (IPA) and diisopropyl ether (DIPE) are compatible with gasoline, they are in the gasoline boiling range and are known to have high blending octane numbers. In addition, by-product propylene from which IPA and DIPE can be made is usually an available refinery feedstock evolving from the production of fuels. The petrochemicals industry also produces mixtures of light olefin streams in the $C_2$ to $C_7$ molecular weight range and the conversion of such streams or fractions thereof to alcohols and/or ethers can also provide products useful as solvents and as blending stocks for gasoline. Therefore, DIPE and IPA production is a commercially practical refinery process.

The catalytic hydration of olefins to provide alcohols and/or ethers is well-established. It is known that propylene and other alkenes can be hydrated over an acidic catalyst to provide isopropanol (IPA) and isoalkanols and di-isopropylether (DIPE) and other di-isoalkylethers.

Various catalytic olefin hydration processes are disclosed in U.S. Pat. Nos. 2,162,913; 2,477,380; 2,797,247; 2,798,097; 2,805,260; 2,830,090; 2,861,045; 2,891,999; 3,006,970; 3,198,752; 3,810,849; and 3,989,762. A representative process is described in U.S. Pat. No. 3,810,849 in which an acid resin catalyst is utilized to convert water and olefins to alcohols. The reaction is conducted at relatively low temperatures, i.e., about 150° C. These acid resin catalysts are unable to tolerate reactivation because of thermal decomposition at reactivation temperatures. Hydrocarbon feedstreams, particularly those containing $C_{3+}$ olefins contain impurities such as nitrogen compounds which react with the acid sites on the resin catalyst and result in aging. When deactivated, the resin catalyst must be discarded which, considering the quantities of material involved, represents not only a costly endeavor, but a significant solid waste disposal problem.

Zeolite-containing catalysts, acidic medium pore and large pore zeolites, developed as alternatives for IPA production. Due to their lower acidity, compared to resin catalysts, zeolites are employed at higher reaction temperatures to achieve the desired conversion rates. These catalyst particles are much more thermally stable than resin catalysts and give no acid effluent, also they can be regenerated by combustion with oxygen.

U.S. Pat. No. 4,214,107, describes hydration of lower linear olefins, in particular, propylene, over a crystalline aluminosilicate zeolite catalyst having a silica-to-alumina mole ratio of at least 12 and a Constraint Index of from 1 to 12, e.g., HZSM-5 type zeolites or zeolite Beta, to provide the corresponding alcohol, essentially free of ether and hydrocarbon by-product.

According to U.S. Pat. No. 4,499,313, an olefin is hydrated to the corresponding alcohol in the presence of hydrogen-type mordenite or hydrogen-type zeolite Y, each having a silica-alumina molar ratio of from 20 to 500. European Patent Application 210,793 describes an olefin hydration process employing a medium pore zeolite as hydration catalyst. Specific catalysts mentioned comprise Theta-1, ferrierite, ZSM-22, ZSM-23 and NU-10.

In general, during hydrocarbon conversion reactions zeolite catalysts become deactivated by the formation of coke, a high molecular weight, hydrogen-deficient species, depositing on the catalyst. The coke deactivates the catalyst by limiting access of the hydrocarbons to the catalytically active acidic sites. Because much of the catalyst deactivation is attributable to the buildup, over time, of this carbonaceous residue on the catalyst, it is important that at least some of the coke be removed for the continuation of cost effective operation.

Because olefin hydration catalysts should provide relatively free access to their internal structure for catalysis of the hydration reactions, deactivation is a particular problem. Oxidative regeneration has been proposed in U.S. Pat. No. 4,214,107 for purposes of restoring catalytic activity.

However, disadvantages associated with oxidative regeneration have made it difficult to implement. The operation is long and must be carefully controlled to avoid thermal degradation of the catalyst. Additionally, oxidative regeneration can lead to loss of catalyst activity because exposure to steam generated during combustion can permanently destroy the catalyst. Because of the difficulties associated with oxidative regeneration and the uncertainty of success in restoring the catalyst, the catalysts are sometimes simply discarded once deactivated through use. This is a costly proposition and creates a solid waste disposal problem. Accordingly, there is a substantial need for a commercially practical olefin hydration catalyst regeneration process.

Passing a reducing gas such as hydrogen over a catalyst bed to remove accumulated coke has been described for certain hydrocarbon conversion catalysts. For Example, in U.S. Pat. No. 4,683,052 a spent noble metal-containing shape selective ZSM-5 or zeolite Beta lube dewaxing catalyst is hydrogen reactivated. The patent teaches that the noble metal-containing catalysts are easily regenerated at pressures less than about 1000 psig and the noble metal is required to increase the extent of coke removed and to permit reactivation at lower temperatures, an important feature since structural damage to non-noble metal-containing dewaxing catalysts was known to occur at higher temperatures. The noble metal, it is proposed, catalyzes removal of carbonaceous residues and inhibits formation of highly refractory carbonaceous residues known as "hard coke" which are not effectively removed from the non-noble metal-containing catalysts.

Since olefin hydration catalysts must allow relatively unconstrained access to their internal structures, any carbonaceous residues remaining on the catalyst after regeneration would undermine the advantages of regeneration. Unlike the dewaxing catalysts, olefin hydration catalysts described here do not employ a noble metal component; thus, the problems associated with hydrogen regenerating the non-noble metal containing dewaxing catalysts would tend to eliminate hydrogen regeneration as an option for these olefin hydration catalysts.

U.S. Pat. Nos. 4,508,836 and 4,358,395 describe regenerating aged coke-selectivated catalysts by contact with hydrogen. These catalysts are coked prior to use to allow relatively constrained access to their internal pore structures. The hydrocarbon conversion reactions in which these catalysts are employed include alkylation, toluene disproportionation and/or isomerization in which the catalyst comprises a crystalline aluminosilicate having a constraint index between about 1 and 12. Since hydrogen regeneration of these catalysts removes only the carbonaceous deposits of the conversion reactions and does not remove the coke deposited on the catalyst during pre-coking, the process has the advantage of eliminating the need for pre-coking after regeneration.

Olefin hydration catalysts are not pre-coked since, as stated previously, they must allow relatively unconstrained access to their internal structure. Thus, the advantages of retaining coke deposits on the catalyst which were realized with hydrogen reactivation of pre-coked catalysts, described in U.S. Pat. Nos. 4,508,836 and 4,358,395, would make hydrogen reactivation of an olefin hydration catalyst an unacceptable procedure.

SUMMARY OF THE INVENTION

We have now discovered that reactivation of an olefin hydration catalyst with a non-oxidizing light gas is commercially practical for regenerating the catalyst. This provides significant advantages over oxidative regeneration.

A feature of the invention is regenerating an olefin hydration catalyst by treating the catalyst with a stream of a light non-oxidizing gas at temperatures and pressures which remove coke and carbonaceous deactivating deposits from the catalyst to restore catalyst activity.

The invention is also related to the production of alcohols employing a catalyst comprising contacting a feedstream comprising an olefin feed and water with the acidic metallosilicate catalyst particles in a reaction zone under olefin hydration conditions.

It is an object of the present invention to regenerate a catalyst used in a process for converting low cost, readily available sources of light olefins to ether(s) which can be used as high octane blending stocks for gasoline.

It is a feature of the invention that at regeneration pressures below about 1000 psig, more specifically, below about 800 psig, there is an unexpected increase in coke removal.

It is an advantage of the invention that hydrogen reactivation of the spent olefin hydration catalyst restores and, in some cases, has been found to enhance ether synthesis activity.

The invention is directed to a process for enhancing ether activity of an olefin hydration catalyst comprising the steps of: contacting an olefin feed with water in an olefin hydration zone with an olefin hydration catalyst of acidic activity whereby said olefin hydration conditions reduce the acidic activity of the catalyst; recovering a product stream containing alcohols and ethers from said olefin hydration zone; regenerating said catalyst under conditions of elevated temperature and pressure by passing a non-oxidizing light gas stream over said catalyst; and returning said regenerated catalyst to the olefin hydration zone whereby said catalyst has enhanced ether synthesis activity.

DETAILED DESCRIPTION OF THE INVENTION

Figure 1:
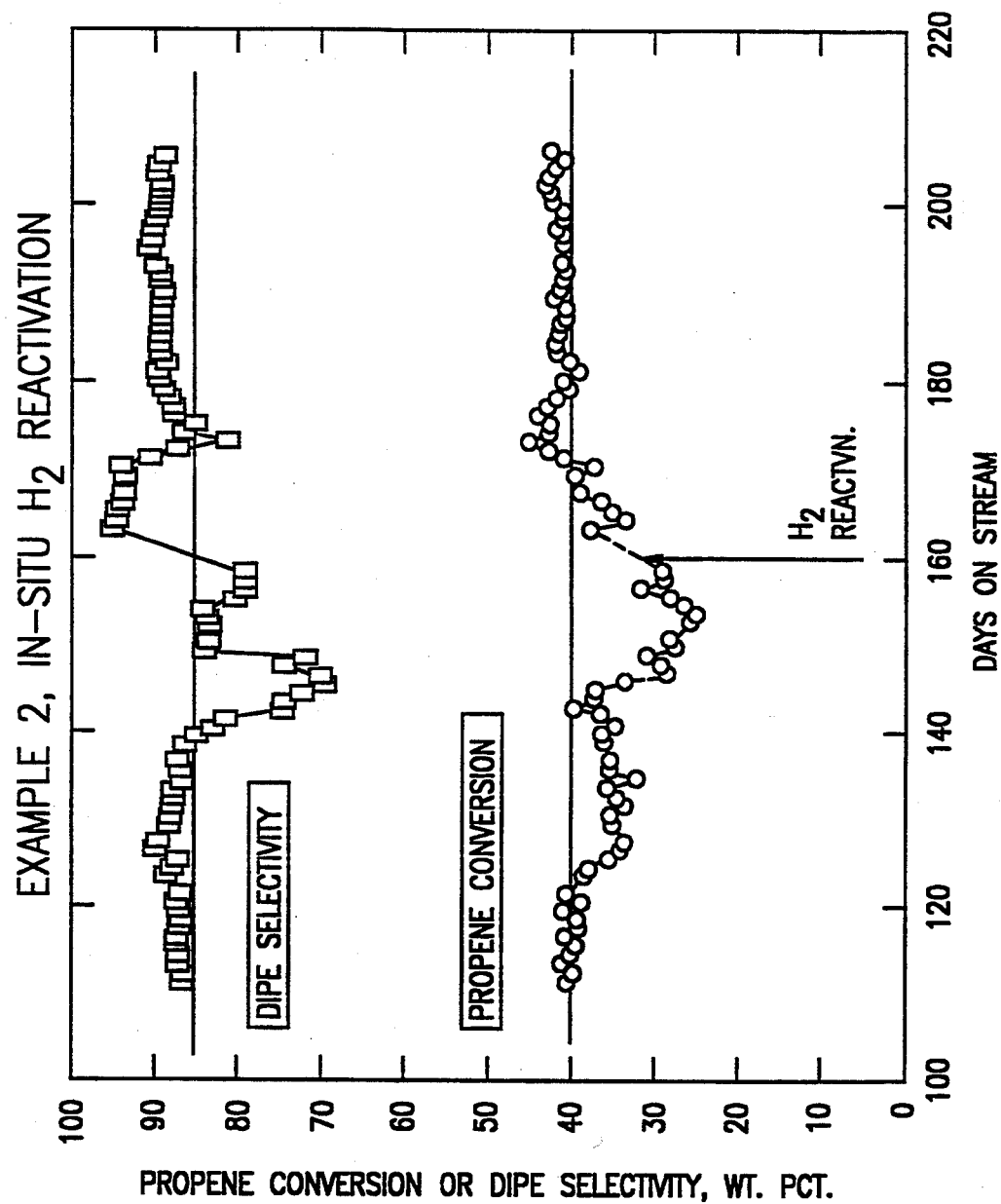
FIG. 1 is a plot of weight % propene conversion or DIPE selectivity versus time (days) on stream.

The addition of alcohols and ethers to gasoline has become a preferred method of increasing the oxygen content of gasoline to make gasoline fuels more environmentally acceptable. One commercial route for the production of alcohols and ethers which are compatible with gasoline, i.e., boiling in the gasoline boiling range, is by the hydration of light olefins. Due to the economics of refinery processes and environmental incentives related to solid waste disposal, it is desirable to develop a method for regenerating an olefin hydration catalyst to extend the process cycle length.

A procedure is disclosed for recovering the initial activity of zeolite-based olefin hydration catalysts. During the reaction of olefins with water to produce IPA and DIPE, the deactivation of zeolitic catalysts presents a difficult problem. However, it has been discovered that the initial activity of the aged zeolite catalysts can be restored with a non-oxidative light gas such as hydrogen.

A number of crystalline materials including zeolite beta have been identified as suitable olefin hydration catalysts. These materials are described in, for example, U.S. Pat. Nos. 4,214,107 and 4,499,313, which also describe the incorporation of a binder made from an oxide of a metal of Group IVA, IIIB and/or IVB. However, a method for regenerating the catalytic material utilized in olefin hydration has not been described.

As employed herein the term regeneration is used interchangeably and synonymously with the term rejuvenation or reactivation when referring to the catalyst regeneration process of the instant invention.

Feedstock

The present invention is applicable to the conversion of individual light olefins and mixtures of light olefins of various structures, preferably within the $C_{2-7}$ range, to alcohols and ethers. Accordingly, the invention is applicable to the conversion of ethylene, propylene, butenes, pentenes, hexenes and heptenes, mixtures of these and other olefins. The preferred olefins are linear but branched and cyclic olefins can be employed. Sources of olefins include gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc.

For example, a typical FCC light olefin stream can possess the following composition:

Typical Refinery FCC Light Olefin Composition

|  | Wt. % | Mole % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.3 |
| Pentanes | 0.7 | 0.4 |

Most specifically, the process of the invention is applicable to the conversion of propylene and propylene-containing streams to mixtures of IPA and DIPE.

Hydration Catalyst

The catalyst of choice comprises a porous acid acting crystalline material. For purposes of this invention, this includes the class of porotectosilicates, i.e., porous crystalline silicates, which contain silicon and oxygen atoms as the major components. Other materials can be present in minor amounts, usually less than 14 mole %, and preferably less than 4 mole %. These components include aluminum, gallium, iron, boron, and the like, with aluminum being preferred. The minor components can be present separately or in mixtures in the catalyst. They can also be present intrinsically in the framework structure of the catalyst.

Representative of this class of acid acting materials are the zeolites. Preferred for use herein as olefin hydration catalysts are zeolite Beta, zeolite X, zeolite L, zeolite Y, ultrastable zeolite Y (USY), dealuminized Y (Deal Y), mordenite, ZSM-3, ZSM-4, ZSM-5, ZSM-12, ZSM-20, ZSM-23, ZSM-35, ZSM-38, ZSM-50, PSH-3, MCM-22 and mixtures of any of the foregoing.

Also included within the definition of the useful zeolites are crystalline porous silicoaluminophosphates such as those disclosed in U.S. Pat. No. 4,440,871, the catalytic behavior of which is similar to that of the aluminosilicate zeolites.

Zeolite Beta is described in U.S. Pat. No. Re. 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192, 3,354,077, 3,375,065, 3,402,996, 3,449,070 and 3,595,611, to which reference is made for details of this catalyst.

Dealuminized zeolite Y (Deal Y) can be prepared by the method found in U.S. Pat. No. 3,442,795, to which reference is made for details of this catalyst.

Zeolite ZSM-3 is described in U.S. Pat. No. 3,415,736, to which reference is made for details of this catalyst.

Zeolite ZSM-5 is described in U.S. Pat. No. Re. 29,948 (of original U.S. Pat. No. 3,702,886), to which reference is made for details of this catalyst.

Zeolite ZSM-12 is described in U.S. Pat. No. 3,832,449, to which reference is made for,the details of this catalyst.

Zeolite ZSM-20 is described in U.S. Pat. No. 3,972,983, to which reference is made for the details of this catalyst.

Zeolite ZSM-23 is described in U.S. Pat. No. 4,076,842, to which reference is made for the details of this catalyst.

Zeolite ZSM-35 is described in U.S. Pat. No. 4,016,245, to which reference is made for the details of this catalyst.

Zeolite ZSM-38 is described in U.S. Pat. No. 4,046,859, to which reference is made for the details of this catalyst.

Zeolite ZSM-50 is described in U.S. Pat. No. 4,640,829, to which reference is made for details of this catalyst.

Zeolite PSH-3 is described in U.S. Pat. No. 4,992,606, to which reference is made for the details of this catalyst.

Zeolite MCM-22 is described in U.S. Pat. Nos. 4,954,325 and 4,992,606 to which reference is made for the details of this catalyst. The use of this zeolite to catalyze the reaction of olefin(s) with water to provide alcohol(s), ether(s) or mixtures thereof is disclosed in U.S. patent application Ser. No. 139,557, filed on Dec. 30, 1987.

In general, the catalyst employed in the olefin hydration process of this invention is, preferably, a large pore zeolite having a framework silica-to-alumina ratio greater than about 7 and a Constraint Index of no greater than about 2, preferably ranging from 0.6 to 2.0.

The framework silica-to-alumina mole ratio is meant to represent, as closely as possible, the ratio of silica to alumina in the rigid anionic framework of the zeolite crystal and to exclude any alumina which may be present in a binder material optionally associated with the zeolite or present in cationic or other form within the channels of the zeolite. Although zeolites with a silica-to-alumina mole ratio of greater than about 7 are useful, zeolites having much higher silica-to-alumina mole ratios, i.e., ratios of at least about 20:1 and greater than about 30:1 can function as olefin hydration catalysts. In addition zeolites as otherwise characterized herein but which are substantially free of aluminum, i.e., zeolites having a silica:alumina mole ratio up to and including infinity, are useful and can even be preferable in some cases.

A convenient measure of the extent to which a zeolite provides controlled access to molecules of varying sizes to its internal structure is the Constraint Index of the zeolite. A zeolite which provides relatively restricted access to, and egress from, its internal structure is characterized by a relatively high value for the Constraint Index, i.e., above about 2. On the other hand, zeolites which provide relatively free access to the internal zeolitic structure have a relatively low value for the Constraint Index, i.e., about 2 or less. The method by which Constraint Index is determined is described fully in U.S. Pat. No. 4,016,218, to which reference is made for details of the method. Constraint Index (CI) values for some known zeolites including several which are outside the scope of the present invention are:

| Zeolite | Constraint Index (At Test Temperature) |
| --- | --- |
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Zeolite Beta | 0.6–2.0 (316° C.–399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with temperature and severity of operation (conversion) and the presence or absence of binders. Likewise, other variables, such as crystal size of the zeolite, the presence of occluded contaminants, etc., can affect the Constraint Index. Therefore, it will be appreciated that it may be possible to so select test conditions, e.g., temperatures, as to establish more than one value for the Constraint Index of a particular zeolite. This explains the range of Constraint Indices for zeolite Beta.

The large pore zeolites which are useful as catalysts in the process of this invention, i.e., those zeolites having a Constraint Index of no greater than about 2, are well known to the art. Representative of these zeolites are zeolite Beta, zeolite X, zeolite L, zeolite Y, ultrastable zeolite Y (USY), dealuminized Y (DeAl Y), mordenite, ZSM-3, ZSM-4, ZSM-12, ZSM-20, ZSM-38, ZSM-50 and mixtures of any of the foregoing.

Although zeolite Beta has a Constraint Index of about 2 or less, it should be noted that this zeolite does not behave exactly like other large pore zeolites. However, zeolite Beta does satisfy the requirements for the olefin hydration catalyst of the present invention. As disclosed in commonly assigned, copending U.S. patent application Ser. No. 336,582, the contents of which are incorporated by reference herein, the use of zeolite Beta to catalyze the hydration of olefins compares favorably with that of other large pore zeolites and as such, may be preferred for use, particularly in the hydration of propylene to provide mixtures of DIPE and IPA.

The zeolite selected for use herein will generally possess an alpha value of at least about 1, preferably at least 10 and more preferably at least about 100. "Alpha value", or "alpha number", is a measure of zeolite acidic functionality The Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an alpha of 1 (Rate constant=0.016 sec$^{-1}$). The Alpha Test is more fully described together with details of its measurement in U.S. Pat. No. 3,354,078, *Journal of Catalysis*, Vol. 4, p. 527 (1965); Vol. 6, p. 278 (1966); and Vol. 61 p. 395 (1980), each incorporated by reference as to that description.

Preferably, the zeolite is an unsteamed high acidity zeolite having framework silica-to-alumina mole ratios ranging from about 35 to 50.

In practicing the olefin hydration process of the present invention, it can be advantageous to incorporate the above-described large pore zeolites into some other material, i.e., a matrix or binder, which is resistant to the temperature and other conditions employed in the process. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

As stated above, in addition to the foregoing materials, the zeolites employed herein are composited with a non-acidic porous matrix material. Materials containing at least one element selected from group IVA, IIIB, and/or IVB of the Periodic Table of Elements (Sergent-Welch Scientific Company, 1979) are typical. Specific examples include carbon, alumina, titania, zirconia, silica, silica-alumina, silica-magnesia, silica-zirconia, silica-thoria, silica-beryllia, silica-titania, etc., as well as ternary oxide composition, such as silica-alumina-thoria, silica-alumina-zirconia, silica-alumina-magnesia, silica-magnesia-zirconia, etc. The matrix can be in the form of a cogel. The relative proportions of zeolite component and matrix material, on an anhydrous basis, can vary widely with the zeolite content ranging from between 1 to about 99 wt %, and more usually in the range of about 5 to about 90 wt %, preferably about 50 to 80 wt. % even more preferably about 70 wt. % of the dry composite.

The binder, usually an inert matrix material such as zircinia, is not expected to influence hydrogen reactivation within the zeolite pores.

In some cases, it may be advantageous to provide the zeolite hydration catalyst as an extrudate bound with a low acidity refractory oxide binder employing the method described in commonly assigned, copending U.S. patent application Ser. No. 44,639, filed May 1, 1987 the contents of which are incorporated by reference herein. In accordance with said method, a homogeneous mixture of a large pore zeolite such as ultrastable zeolite Y (USY) or zeolite Beta, water and a low acidity refractory oxide binder, e.g., silica, which contains at least an extrusion-facilitating amount of the binder provided in a colloidal state and which is substantially free of added alkali metal base and/or basic salt, is formed into an extrudable mass, the mass is extruded and the resulting extrudate is dried and calcined.

The original cations associated with the zeolite utilized herein can be replaced by a wide variety of other cations according to techniques well known in the art, e.g., by ion-exchange. Typical replacing cations include hydrogen, ammonium, alkyl ammonium and metal cations, and their mixtures.

A typical ion-exchange technique involves contacting the particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249; 3,140,251 and 3,140,253.

Following contact with a solution of the desired replacing cation, the zeolite is then preferably washed with water and dried at a temperature ranging from 150° to about 600° F. and thereafter calcined in air or other inert gas at temperatures ranging from about 500° to 1500° F. for periods of time ranging from 1 to 48 hours or more.

HYDRATION CONDITIONS

For acceptable results to be achieved, the conditions of olefin hydration must be maintained within relatively narrow limits. Suitable operating conditions include a temperature of ambient to about 300° C., preferably from about 50° C. to about 220° C. and more preferably about 90° to 200° C., a total system pressure of at least about 50 atm, preferably at least about 75 atm and more preferably at least about 100 atm, a water to total olefin mole ratio of from about 0.1 to less than about 1.0, preferably from about 0.1 to 0.8 and most preferably from about 0.15 to 0.5.

Those skilled in the art will recognize that selection of specific conditions for a particular feed will influence product distribution. It will also be appreciated that the precise conditions selected will in some measure reflect the nature of the olefin feed, isoolefins generally requiring milder process conditions than straight chain olefins.

The olefin hydration process of this invention can be carried out under liquid phase, vapor phase or mixed vapor-liquid phase conditions in batch or continuous manner using a stirred tank reactor or fixed bed flow reactor, e.g., trickle-bed, liquid-up-flow, liquid-downflow, counter-current, co-current, etc. Reaction times of from about 20 minutes to about 20 hours when operating in batch and a liquid hourly space velocity (LHSV) of from about 0.1 to about 10 when operating continuously are suitable. It is generally preferable to recover any unreacted olefin and recycle it to the reactor.

When seeking to maximize the production of ether by the hydration of olefin, the aqueous product effluent from the olefin hydration reactor containing both alcohol and ether olefin hydration products can be introduced into an extractor, for recovery of ether. The dilute aqueous solution of alcohol from the extractor may be then introduced into a distillation column, where a water/alcohol azeotrope is recovered for recycle to the hydration reactor for further alcohol conversion to ether, if desired.

A particularly advantageous procedure for producing mixtures of alcohol and ether, and in particular IPA and DIPE, from the hydration of an olefin-containing feed (a propylene-containing feed in the case of IPA/DIPE mixtures) employing a large pore zeolite such as zeolite Y or zeolite Beta is described in commonly assigned, U.S. Pat. No. 4,857,664 to which reference is made for a disclosure of the procedure.

Catalyst Regeneration

The process includes recovery of the initial activity of the aged zeolite-based olefin hydration catalyst. Catalyst reactivation is achieved by contacting the spent catalyst particles with a non-oxidizing light gas, preferably a reducing gas such as hydrogen. Other gases which may work are methane and carbon monoxide. The gas is contacted with the spent catalyst in a regeneration zone under conditions of temperature and pressure sufficient to remove at least a major amount of impurities from the catalyst. Typical regeneration conditions include temperatures ranging from about 150° C. to about 550° C. (302° F. to 1022° F.), preferably from about 250° C. to about 500° C. (482° F. to 932° F.), and most preferably from about 300° C. to 450° C. (572° F. to 842° F.). The amount of time necessary to complete the regeneration can range from about 8 to 120 hours, preferably from about 16 to 72 hours. The flow rate of the regenerating gas can range from between about 10 to 1000 volume of gas per volume of catalyst per hour (cc/cc catalyst), preferably from about 100 to about 800 cc/cc catalyst, and more preferably from about 200 cc/cc catalyst to about 500 cc/cc catalyst and even more preferably from 300 to 400 cc/cc catalyst. Typically, pressures range from about 101.35 kPa to about 6900 kPa (0 psig to 1000 psig) preferably below about 5500 kPa (800 psig), more preferably from below about 4200 kPa (600 psig) and even more preferably from 790 kPa to 2,859 kPa (100–400 psig). It was found that at the lower pressures greater coke removal was achieved.

Prior to regenerating, the flow of feed to the reactor is discontinued. The catalyst is dried with an inert gas such as nitrogen, methane or propane. To dry the catalyst, the temperature of the reactor is raised to about 90° C. to 200° C. (194° F. to 392° F.), preferably from about 120° C. to about 180° C. (248° F. to 356° F.) at low pressures, preferably ranging from about 14 kPa (2 psia) to about 200 kPa (30 psia), most preferably from about 30 kPa (5 psia) to about 100 kPa (15 psia). Thereafter the reactor is purged with an inert gas such as nitrogen.

The sources of hydrogen for the regeneration step can be from other refinery processes, catalytic reformer, dehydrogenation processes, hydrogen plant, hydrogen recycle or other suitable sources.

The olefin hydration catalyst regeneration will remove almost all the coke deposited on the catalyst, particularly, more than about 50 wt. %, preferably more than about 70 wt. % and more preferably more than about 80 wt. % and even as high as 90 wt. %. Greater than about 50% of the catalyst activity will be restored, preferably greater than about 60%, more preferably greater than about 70%.

The following examples are illustrative of the olefin hydration process of the present invention. In all of the examples, the olefin hydration catalyst was zirconia bound zeolite beta.

EXAMPLE 1

Hydrogen treatment of a sample of an aged olefin hydration catalyst (less than 1 gm) was performed ex situ in a small scale high pressure weight balance. The catalyst lost 40° F. in propene conversion activity over 150 days on stream. Hydrogen gas was pumped into the reactor containing the spent catalyst. The treatment was conducted at 750° F., 600 psig, 100% hydrogen flow for 12 hours. Significant coke removal in excess of 90 wt. % of the deposited coke was observed.

EXAMPLE 2

The hydrogen treatment of an aged catalyst which deactivated during the course of 150 days on stream from providing 40 to 50% propene conversion to providing 20 to 25% conversion was performed in situ. The temperature of the reactor was raised to 300° F., 0 psig, to dry the catalyst. The reactor was purged with nitrogen, an inert gas, at 8.5 SCFH $N_2$/lb catalyst for 24 hours. During nitrogen purge, the pressure was increased to 600 psig. Nitrogen flow was discontinued.

Hydrogen flow was established at 8.5 SCFH $H_2$/lb catalyst and the pressure was maintained at 600 psig. During hydrogen flow, the reactor temperature was raised to 700° F. at 50° F./hour. The temperature was further increased to 850° F. under a hydrogen flow at 25° F./hour. The temperature was maintained at 850° F., hydrogen flow of 8.5 SCFH/$H_2$/lb catalyst and a pressure of 600 psig for 72 hours. Hydrogen flow was maintained and reactor pressure was maintained at 600 psig while the temperature was lowered to below 150° F. After 16 hours, hydrogen flow was discontinued. The reactor was purged with nitrogen, an inert gas, at a flow of 4 SCFH/lb catalyst and the pressure was lowered to 0 psig.

A plot of propene conversion or DIPE selectivity (DIPE product/DIPE and oligomer product) versus time (days) on stream is presented in FIG. 1. FIG. 1 clearly shows the decline and recovery in propene conversion before and after the hydrogen reactivation. It was noted that the hydrogen reactivation also increased catalyst DIPE selectivity.

The amount of carbon and hydrogen on the catalyst was determined by standard techniques and it was noted that the amount of carbon and hydrogen on the catalyst was significantly lower after hydrogen reactivation. The following Table 1 presents a comparison between samples of the catalyst before and after the hydrogen treatment.

TABLE 1

|  | Before Reactivation | After Reactivation |
|---|---|---|
| Carbon on sample, wt. % | 5.8 | less than 1.0 |
| Hydrogen on sample, wt. % | 1.0 | 0.7 |
| Total carbon and hydrogen, wt. % | 6.8 | less than 1.7 |

Additionally, it was noted that the reactor temperature requirement needed to maintain a constant 40% propene conversion was lower. For example, the reactor temperature required for 40% propene conversion versus time on stream was 365° F. before the reactivation. The temperature was reduced to 325° F. after the reactivation.

Figure 2:
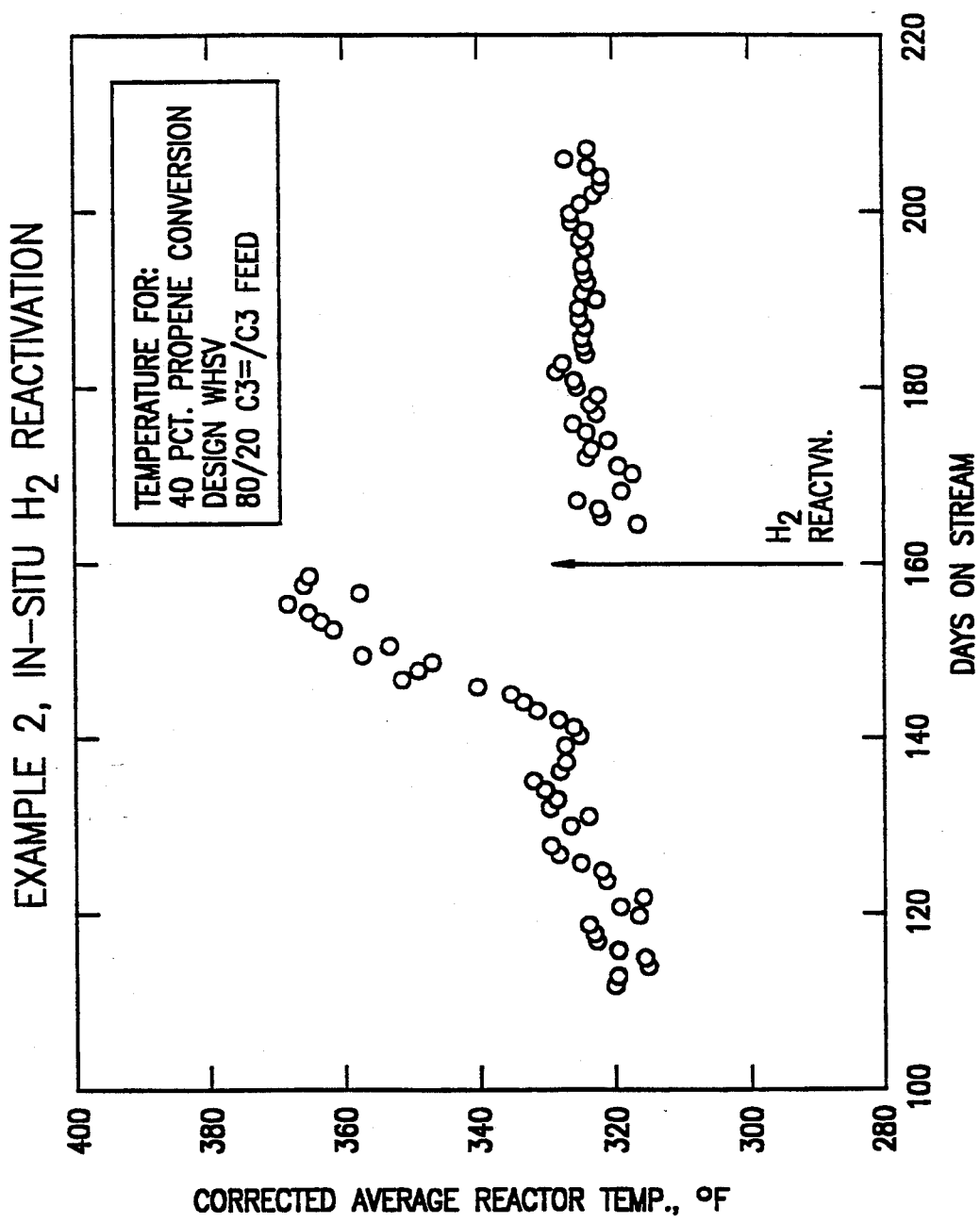
FIG. 2 is a plot of corrected average reactor temperature (°F.) versus time (days) on stream for 40% conversion of propene to DIPE before and after hydrogen reactivation.

FIG. 2 is a plot of the average reactor temperature in °F. versus days on stream required to maintain a 40% propene conversion. FIG. 2 shows that the average temperature required to maintain the 40% conversion was between about 300° and 325° F. until about 140 days on stream. At about 160 days on stream the reactor temperature required to maintain 40 wt. % conversion was 370° F.

After reactivation with hydrogen, almost all the original catalyst activity was restored so that 40 wt. % conversion was maintained at about 325° F.

The following comparative example describes an attempt to reactivate a spent olefin hydration catalyst by treatment with nitrogen, an inert gas.

EXAMPLE 3

An aged catalyst which deactivated during the course of 120 days on stream was loaded in a reactor and purged with nitrogen flow of 37 SCFH $N_2$/lb catalyst. The temperature of the reactor was raised to 700° F. at 180° F./hr and 0 psig while maintaining the $N_2$ flow. The temperature was maintained at 700° F. and nitrogen flow of 37 SCFH $N_2$/lb catalyst for 3 hours. Then the reactor temperature was lowered to room temperature under nitrogen flow of 37 SCFH $N_2$/lb catalyst. This reactivated catalyst was tested for conversion of isopropanol (IPA) to diisopropyl ether (DIPE) and was found to have no measurable improvement on the performance of the catalyst.

Figure 3:
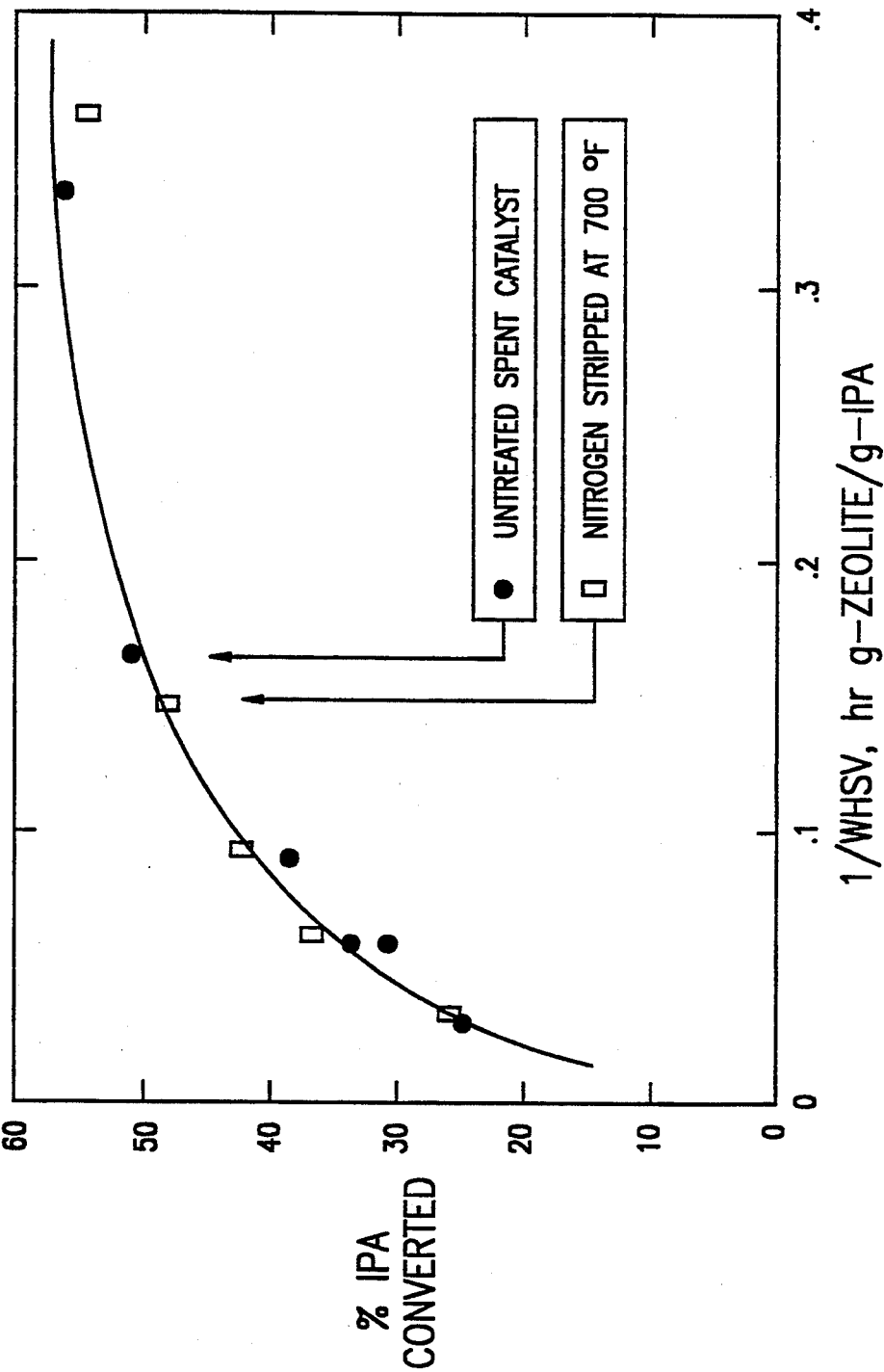
FIG. 3 is a plot of conversion of IPA (%) to DIPE versus IPA feed space time utilizing a nitrogen stripped spent catalyst and an untreated spent catalyst.

FIG. 3 shows a plot of the wt. % conversion to DIPE versus the feed rate (expressed in terms of IPA feed space time) in the presence of both the untreated spent zeolite beta and the nitrogen stripped zeolite beta described in Example 3. It was noted that the conversion activity was similar for both catalysts.

The following example illustrates the test procedure used to evaluate the activity of catalysts of Examples 5 to 10.

EXAMPLE 4

The activity of the catalysts was assessed, in an IPA catalyst test in which isopropyl alcohol (IPA) was converted to DIPE product and water in a liquid phase, isothermal, fixed bed tubular reactor operated at 1000±10 psig and 160±2° C. and various feed rates of pure IPA. Typically, 2 to 3 g catalyst was distributed in sand in an 8 cc section of the ⅜-inch diameter reaction zone.

Activities of the spent and regenerated catalyst are compared by noting the contact time required for a given conversion. For example, for 40% conversion, spent catalyst requires a contact time of about 0.8 hour while after the hydrogen regeneration 40% conversion requires a contact time of about 0.1 hour; therefore, the hydrogen treatment improves activity about 8-fold.

The activity of a catalyst was quantified by comparing the WHSV required for a specified IPA reference conversion level with the WHSV required for the test catalyst conversion level. A fresh catalyst was chosen as a reference catalyst and for purposes of comparison, a reference conversion level of 53% was arbitrarily selected. Determination of the activity of a hydrogen regenerated catalyst (of Example 5) is demonstrated below.

Figure 4:
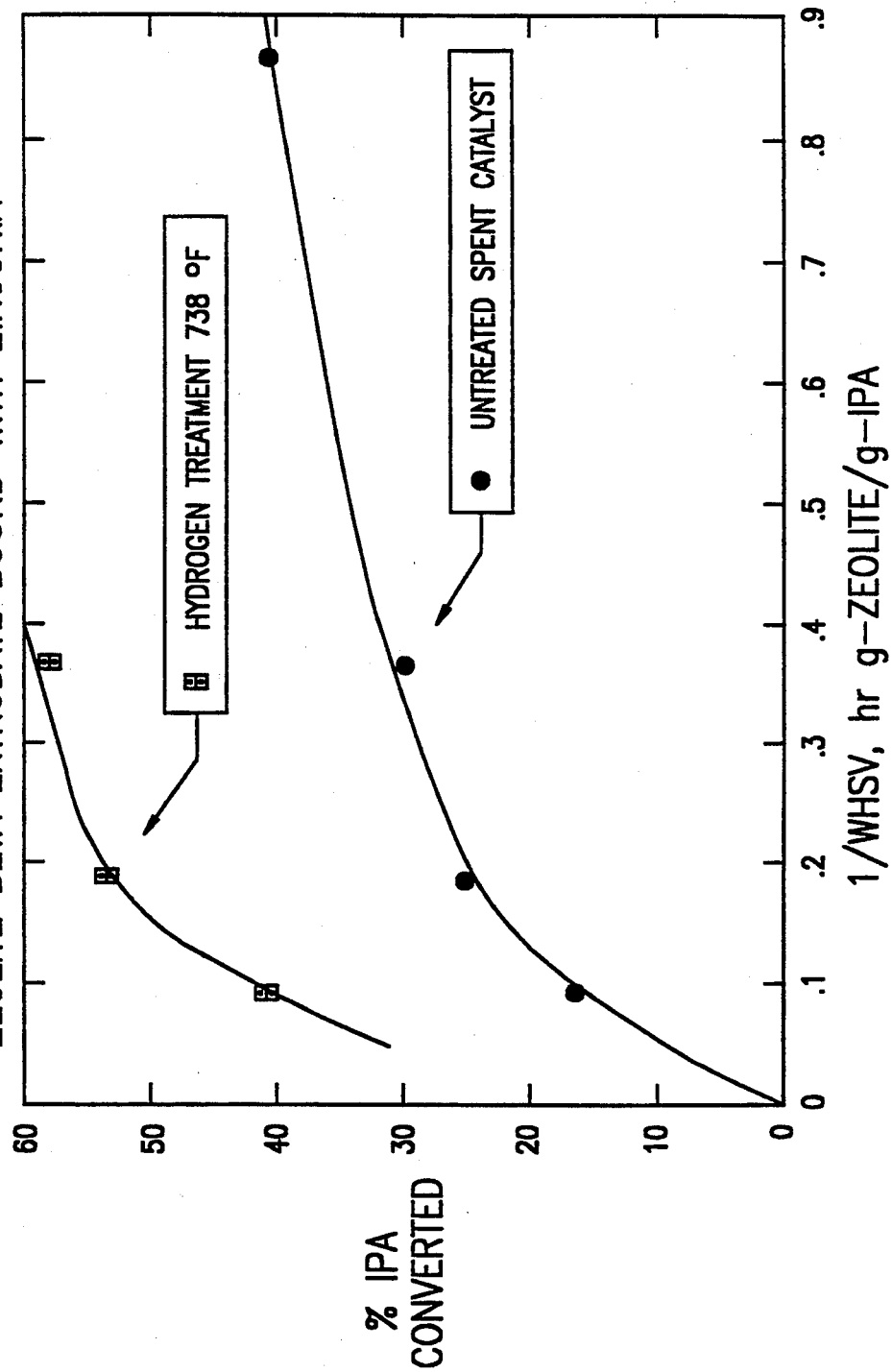
FIG. 4 is a plot of conversion of IPA to DIPE versus IPA feed space time comparing a hydrogen reactivated spent catalyst with an untreated spent catalyst.

FIG. 4 is a plot of % IPA converted vs. feed space time for both a hydrogen regenerated catalyst and a spent catalyst. The hydrogen regenerated catalyst achieved 53% conversion at 0.19 hour which corresponds to a WHSV of 5.3. For a fresh catalyst sample (the reference catalyst, not shown in FIG. 4), the IPA test data were interpolated using a plot like that of FIG. 4 to find 53% conversion at 8.8 WHSV. Thus, the activity of the hydrogen regenerated catalyst of relative to fresh was 100×5.3/8.8=60%. In the case of a spent catalyst, conversion was lower than 53%. Therefore, to determine the activity of this material, a reference conversion level of 20% was selected for purposes of finding the WHSV for this sample as well as the reference catalyst. The activities of the catalysts of the examples were calculated in the foregoing matter and listed in Table 2.

DIPE catalyst was aged in a pilot plant run. The reactor consisted of three adiabatic reaction sections. Catalyst samples from the top of the first reaction section (Zone 1) and the bottom of the first reaction section (Zone 8) were removed after 75 days of operation. Zone 1 catalyst contained 8% coke and Zone 8 catalyst contained 4% coke. Portions of these samples were subjected to the hydrogen and oxidative regeneration as described in the following Examples.

EXAMPLE 5

A 3 gm sample of a catalyst taken from Zone 1 was assessed using the IPA catalyst test described in Example 4.

The sample was flushed with nitrogen, cooled, and regenerated by treatment with hydrogen flowing at 800 cc/hr g-catalyst and a pressure of 1000 psig. Treatment temperature was increased from room temperature (about 68° to 77° F.) to 738° F. over about 5 hours and held at this temperature for 17 hours. After treatment the sample was purged in nitrogen and cooled. Regenerated activity was then assessed by the IPA test described above. This regenerated catalyst was designated Catalyst A. Results are presented in FIG. 4.

FIG. 4 is a plot of IPA conversion to essentially DIPE verses contact time as measured by 1/WHSV based on the hourly feed rate of IPA per gram of zeolite in the catalyst. Activities of the spent and regenerated catalyst can be compared by noting the contact time required for a given conversion in each case. For example, for 40% conversion, the spent catalyst requires a contact time of about 0.85 hour. By comparison, after the hydrogen regeneration the same 40% conversion was achieved at about 0.1 hour. Thus, hydrogen treatment improved activity about 8-fold. Unlike the nitrogen stripping case of Example 3 and FIG. 3, hydrogen stripping results in a significant spent catalyst activity improvement.

EXAMPLE 6

An aged olefin hydration catalyst from Zone 1 was hydrogen regenerated as described in Example 5 with the following exceptions: hydrogen gas flow rate of about 500 cc/hr.g-catalyst. The temperature during gas flow was gradually raised from room temperature (about 20° to 25° C.) to a temperature of 750° F. at 600 psig for 17 hours. The regenerated catalyst was designated catalyst B.

EXAMPLE 7

An aged olefin hydration catalyst from Zone 8 was hydrogen regenerated as described in Example 6 with the following exceptions: the temperature during gas flow was maintained at 850° F. for 72 hours. The regenerated catalyst was designated catalyst C.

EXAMPLE 8

An aged olefin hydration catalyst from Zone 8 was hydrogen regenerated as described in Example 6. The catalyst was designated catalyst D.

The following comparative examples illustrate oxidative regeneration of aged catalysts.

EXAMPLE 9

An aged catalyst from Zone 1 was calcined in air at 950° F. and atmospheric pressure for 2 hours, cooled and exchanged three times in 25 ml 1N ammonium nitrate solution per gram catalyst and again air calcined at 950° F., 1 atm. for 2 hours. This is the maximum extent to which spent catalyst can be regenerated by oxidative removal of coke and exchange of accumulated cation poisons. This catalyst was designated catalyst E.

EXAMPLE 10

An aged catalyst from Zone 8 was calcined following the procedure of Example 9.

TABLE 2

| Catalyst | Activity of DIPE Catalyst | | |
|---|---|---|---|
| | Flow Rate | Time (hr) | % Activity |
| Fresh Catalyst | | | 100 |
| H$_2$ Regenerated Catalyst | | | |
| Zone 1, 8% coke | | | |
| A (738° F., 1000 psig) | 800 | 17 | 60 |
| B (750° F., 600 psig) | 500 | 17 | 80 |
| Zone 8 | | | |
| C (850° F., 600 psig) | 500 | 72 | 80 |
| D (750° F., 600 psig) | 500 | 17 | 80 |
| Oxidatively Regenerate Catalyst | | | |
| Zone 1 | | | |
| E (950° F., 1 atm) | | | 80 |
| Zone 8 | | | |
| F (950° F., 1 atm) | | | 80 |
| Spent Catalyst | | | |
| Zone 1 | | | |
| G | | | 8 |
| Zone 8 | | | |
| H | | | 52 |

These data show that hydrogen regeneration can restore catalyst activity to a level which is comparable to that of the more difficult and elaborate oxygen regeneration procedure.

Furthermore, the data show the criticality of reaction pressure in that reaction pressures below about 1000 psig are more effective in restoring catalyst activity.

The following Examples demonstrate hydrogen regeneration of a catalyst aged over 145 days on stream. These examples also demonstrate the extension of catalyst life by successive hydrogen regeneration treatments and the use of a hydrogen recycle stream to regenerate the catalyst.

EXAMPLE 11

A catalyst which had been on stream for 145 days and which went from greater than 40% propene conversion to about 20% conversion was regenerated with hydrogen in-situ.

The reactor temperature was raised to 300° F. at 0 psig to dry the aged catalyst. The reactor was purged with nitrogen at 8.5 SCFH N$_2$/lb catalyst for 24 hours. Nitrogen flow was discontinued and the reactor was pressurized to 250 psig with hydrogen. Fresh hydrogen gas flow was established at 0.5 SCFH H$_2$/lb catalyst and hydrogen recycle gas flow was established at 8.0 SCFH H$_2$/lb catalyst. The temperature was raised from 50° F./hour to 500° F. The conditions were maintained at 500° F. for 24 hours. The reactivation was temporarily terminated by lowering the reactor temperature to ambient temperatures (about 20° to 25° C.) over a period of 16 hours. Fresh hydrogen flow (0.5 SCFH H$_2$/lb catalyst) and 250 psig pressure was maintained as the temperature was lowered. After 16 hours fresh hydrogen flow was discontinued and the reactor depressured to 0 psig, and purged with nitrogen at 4 SCFH/lb catalyst. A small sample of catalyst designated catalyst I was withdrawn for analysis of carbon content. The results are reported in Table 3.

EXAMPLE 12

The reactor was re-pressurized with hydrogen to 250 psig, fresh hydrogen flow was established at 0.5 SCFH H$_2$/lb catalyst, recycle gas flow was established at 8.0 SCFH/lb catalyst, and the temperature was raised at 50° F./hour to 750° F. The conditions were maintained at 750° F. for 30 hours., The reactivation was finally terminated by lowering the temperature to ambient (about 20° to 25° C.) over a 16 hour period. Fresh hydrogen flow (0.5 SCFH H$_2$/lb catalyst) and 250 psig pressure was maintained as the temperature was lowered. After 16 hours fresh hydrogen flow was discontinued and the reactor pressure was reduced to 0 psig and purged with nitrogen at 4 SCFH/lb catalyst. A small sample of this catalyst designated catalyst J was withdrawn for analysis of carbon content. The results are reported in Table 3.

TABLE 3

| Catalyst | Carbon Content of Catalyst | | |
|---|---|---|---|
| | Spent | I | J |
| Carbon, wt. % | 7.6 | 3.2 | 0.15 |
| Carbon removed, % | — | 58.0 | 98.0 |

EXAMPLE 13

Figure 5:
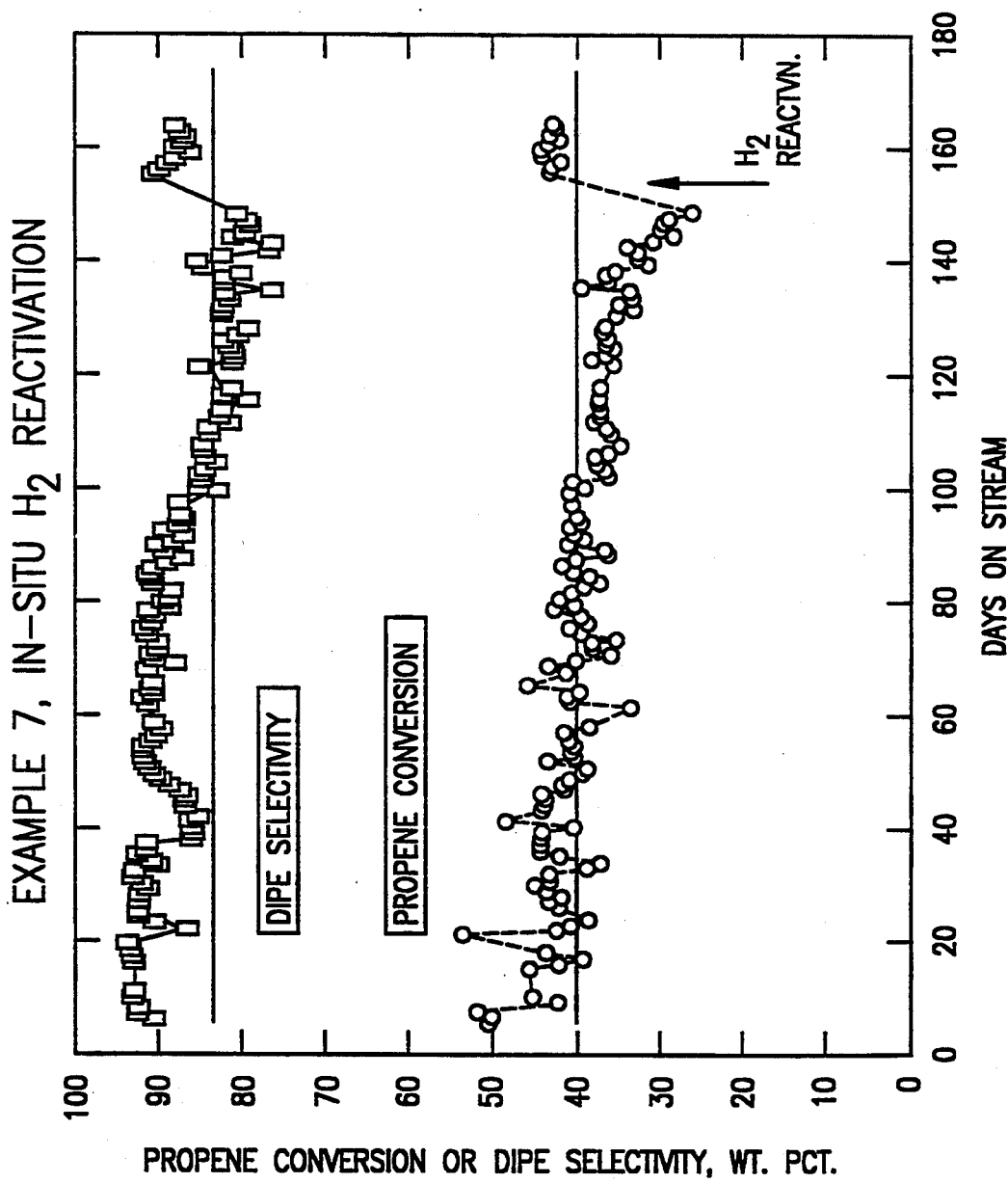
FIG. 5 is a plot of weight % propene conversion and DIPE selectivity versus time (days) on stream.

After final reactivation the catalyst was placed back on stream for DIPE production. A plot of propene conversion or DIPE selectivity (DIPE product/DIPE+oligomer product) versus time (days) on stream is shown in FIG. 5. FIG. 5 clearly shows the performance recovery before and after the hydrogen reactivation in terms of both propene conversion and DIPE selectivity.

Figure 6:
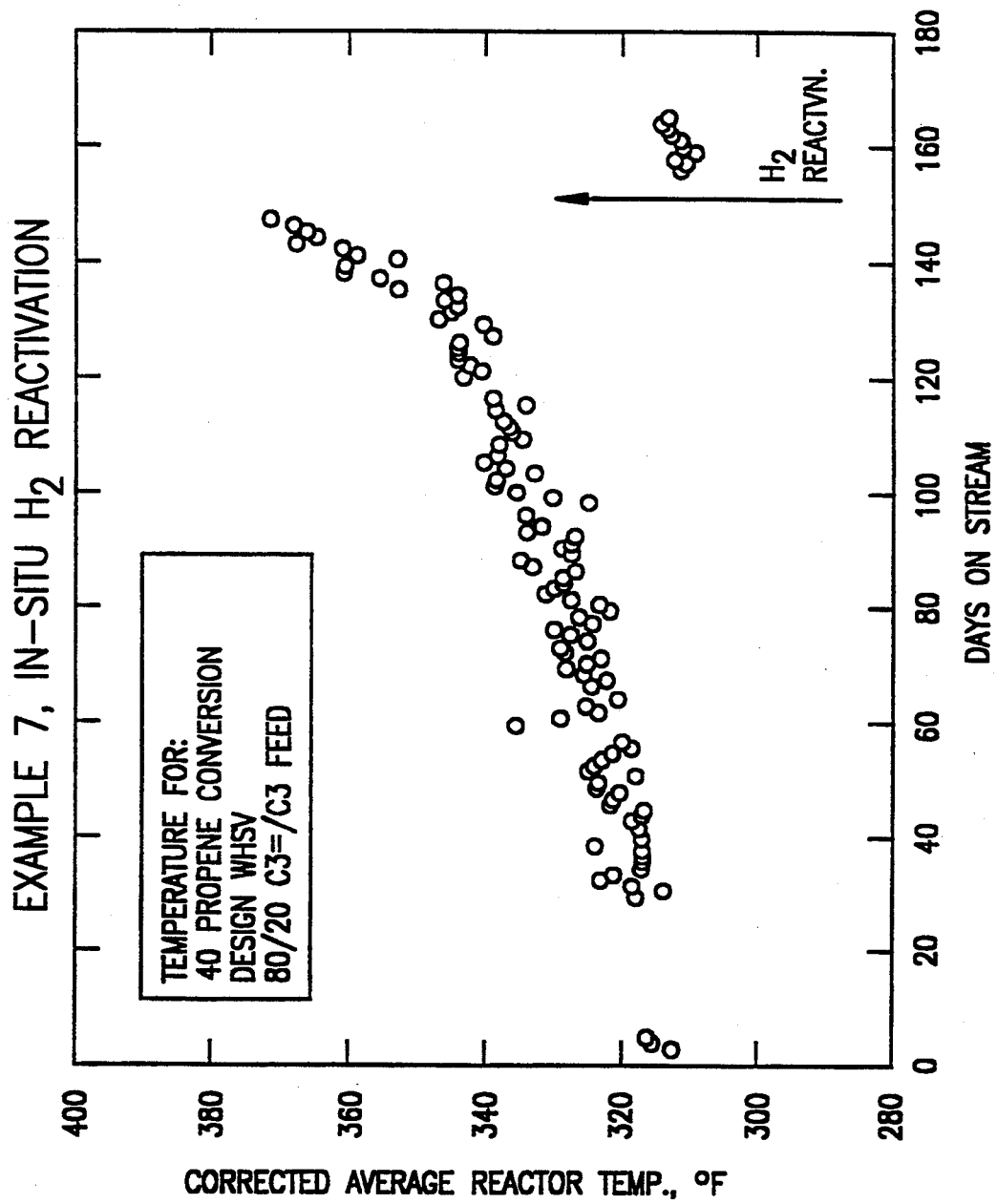
FIG. 6 is a plot of corrected average reactor temperature (°F.) versus days on stream for 40% conversion of propene to DIPE before and after hydrogen reactivation.

FIG. 6 shows a plot of average reactor temperature required to maintain approximately 40% propene conversion versus time (days) on stream. This plot also shows the activity recovery from hydrogen regeneration as the reactor temperature necessary to maintain 40% conversion declined from about 370° F. prior to the hydrogen regeneration to about 315° F. after regeneration with hydrogen.

The following Examples 14 and 15 lend further support to our finding that lower reaction pressures are more effective in removing coke than higher reaction pressures.

EXAMPLE 14

An aged olefin hydration catalyst containing 8 wt. % coke from Zone 1 (Example 4) was hydrogen reactivated ex-situ in a small scale weight balance capable of high pressure operation. Experiments were conducted at the temperatures and pressures reported below in Table 4. In each experiment, a 1–2 gm sample of aged catalyst was dried under flowing N$_2$ at 200° F. for 4–5 hours at the desired pressure and then the gas flow changed to hydrogen. The catalyst was then heated in 1 hour to the desired hydrogen reactivation temperature under flowing hydrogen and held for the reactivation period. Coke removal results are reported in Table 4.

EXAMPLE 15

Figure 7:
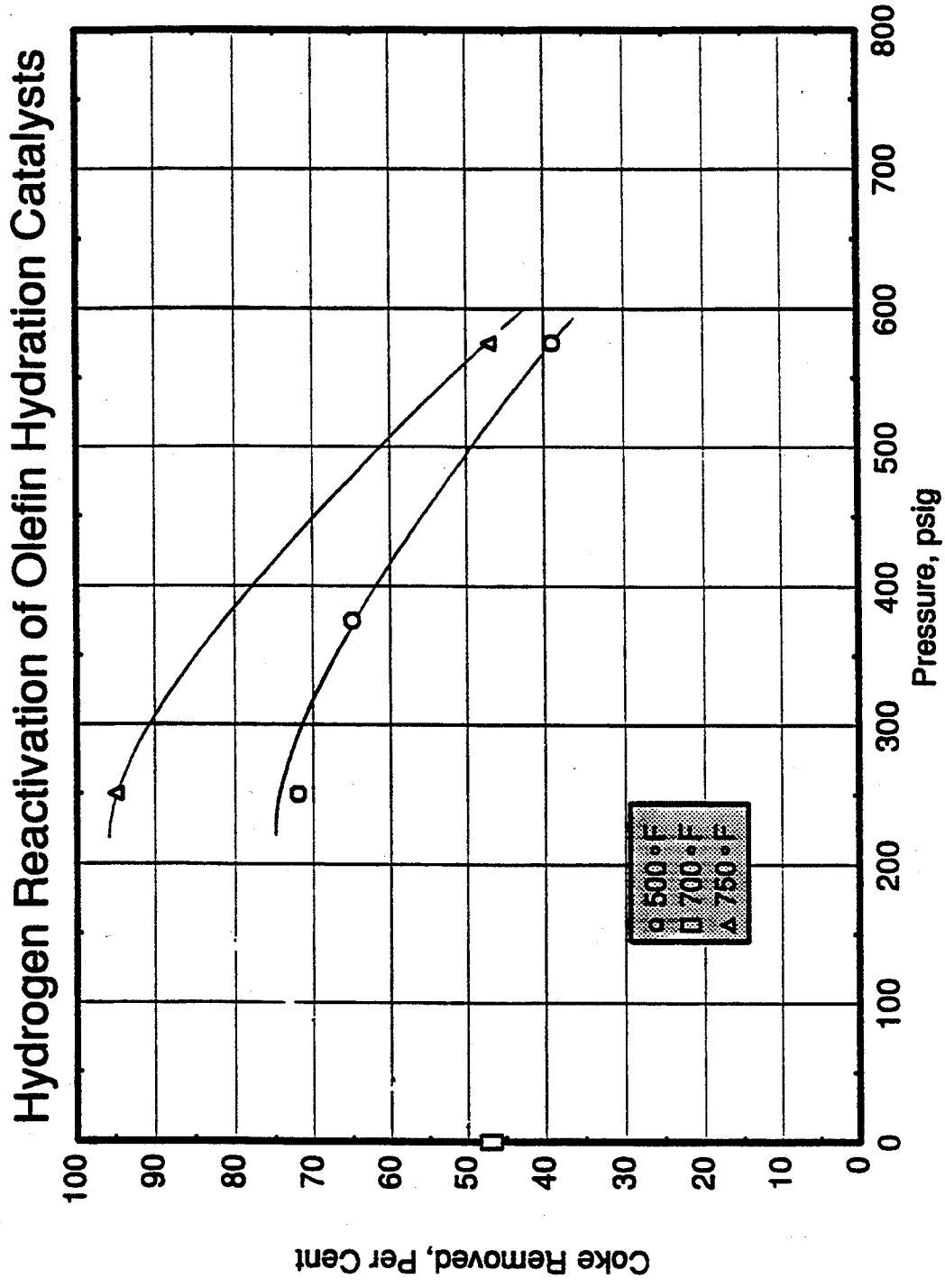
FIG. 7 is a plot of pressure versus percent coke removal.

An aged olefin hydration catalyst containing 4.9 wt. % coke which had deactivated during the course of 125 days on stream hydrating propylene to IPA and DIPE was hydrogen reactivated exsitu in a small scale weight balance at atmospheric pressure. The catalyst was heated to 700° F. under flowing hydrogen and held for 3 hours. Coke removal results are reported in Table 4. Results from Examples 14 and 15 are plotted in FIG. 7 showing an unexpected maximum in coke removal effectiveness as a function of pressure.

TABLE 4

| | Example 14 | Example 14 | Example 14 | Example 14 | Example 14 | Example 15 |
|---|---|---|---|---|---|---|
| Aged Catalyst Coke Content, wt. % | 8 | 8 | 8 | 8 | 8 | 4.9 |
| Treatment Conditions | | | | | | |
| H$_2$ pressure, psig | 250 | 375 | 575 | 250 | 575 | 0 |
| Temperature, °F. | 500 | 500 | 500 | 750 | 750 | 700 |
| % Coke Removal | 72 | 65 | 39 | 95 | 47 | 47 |

What is claimed is:

1. A process for enhancing ether synthesis activity of an olefin hydration catalyst comprising the steps of:
    contacting an olefin feed with water in an olefin hydration zone with an olefin hydration catalyst comprising zeolite beta and a zirconia binder whereby said olefin hydration conditions reduce the acidic activity of the catalyst;
    recovering a product stream containing alcohols and ethers from said olefin hydration zone;
    regenerating said catalyst in one-stage under conditions of elevated temperatures ranging from about 150° C. to about 550° C. and pressure below about 800 psig by passing a hydrogen gas stream over said catalyst;
    terminating the hydrogen regenerating step; and resuming contact of the olefin hydration catalyst with the olefin feed and water, the catalyst having enhanced ether synthesis activity.

2. The process of claim 1 in which the olefin feed comprises propylene.

3. The process of claim 1 in which the regeneration condition of pressure ranges from 0 to 800 psig.

4. The process of claim 1 in which the regeneration condition of pressure is from about 0 to 600 psig.

5. The process of claim 1 in which the regeneration condition of pressure is from about 100 to 400 psig.

6. The process of claim 1 in which the olefin feed is a mixture of olefins containing from two to seven carbon atoms.

7. The process of claim 1 in which the olefin feed contains at least one olefin selected from the group consisting of ethylene, propylene, butene, pentene, hexene and heptene.

8. The process of claim 1 in which the olefin feed is a gas plant off-gas containing light olefins.

9. The process of claim 1 in which the hydrogen gas stream comprises a hydrogen recycle stream.

10. The process of claim 9 in which the hydrogen gas stream further comprises a fresh hydrogen gas stream.

* * * * *